United States Patent [19]
Sato et al.

[11] Patent Number: 4,909,942
[45] Date of Patent: Mar. 20, 1990

[54] PROCESS FOR REMOVING PYROGENS

[75] Inventors: Tadashi Sato, Takatsuki; Taizo Watanabe, Nagaokakyo; Satoshi Minobe, Ohtsu; Takashi Nishimura, Amagasaki; Masahiro Kagotani, Himeji; Tomonobu Ase, Yokohama; Zenjiro Honda, Toyonaka; Shinji Nagamatsu, Himeji, all of Japan

[73] Assignees: Tanabe Seiyaku Co., Ltd.; Daicel Chemical Industries, Ltd., both of Osaka, Japan

[21] Appl. No.: 256,729

[22] Filed: Oct. 12, 1988

[30] Foreign Application Priority Data

Oct. 16, 1987 [JP] Japan .................. 62-261370
Sep. 5, 1988 [JP] Japan .................. 63-221877

[51] Int. Cl.$^4$ ................. B01D 13/00
[52] U.S. Cl. ..................... 210/651; 210/259
[58] Field of Search ................ 422/88; 210/651, 259

[56] References Cited

U.S. PATENT DOCUMENTS 4,261,834  4/1981  de Winter ............... 210/651
4,412,985  11/1983  Shanbrom ............... 424/88 X
4,610,790  9/1986  Reti et al. ............... 210/259 X Primary Examiner—Frank Spear
Attorney, Agent, or Firm—Flynn, Thiel, Boutell & Tanis

[57] ABSTRACT

Pyrogens are removed out of a solution thereof by (1) treating the solution with a membrane and then (2) treating the resulting solution with a pyrogen adsorbent. The obtained solution is useful in pharmaceutical fields.

15 Claims, 2 Drawing Sheets

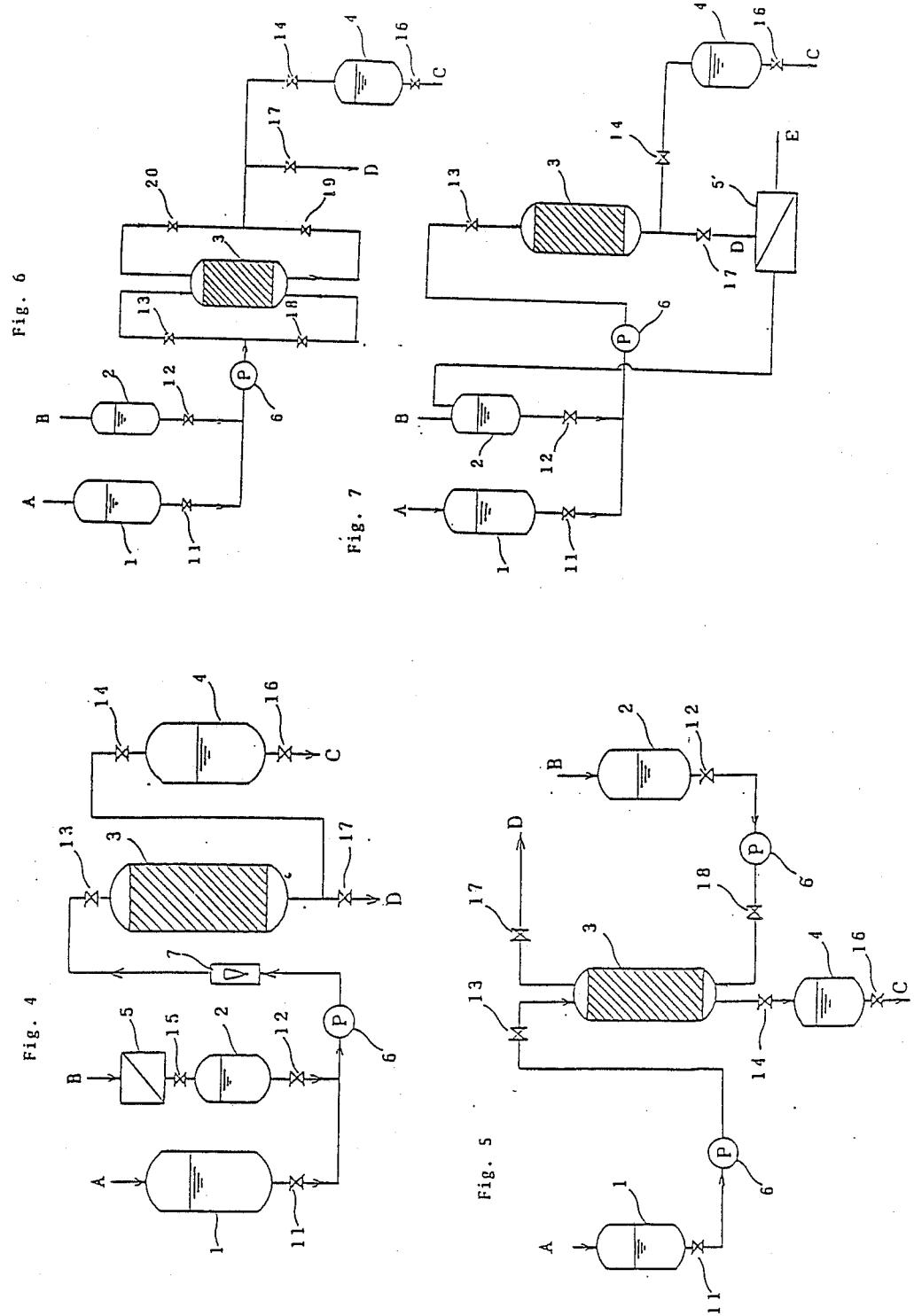

PROCESS FOR REMOVING PYROGENS

This invention relates to a process for removing pyrogens from a pyrogen-containing solution by using a membrane together with a pyrogen adsorbent.

More particularly, the present invention relates to a process for preparing a pyrogen-free solution. The pyrogen-free solution prepared according to the present invention is available for medicinal uses, for example, as a dialysate for treating those who suffer from renal insufficiency, as a replenishing fluid for an artificial kidney of filtration type, as a diluent for an instillation drug of a high concentration for bedside uses, in washing various medical instruments, in the preparation of drugs such as purified water for injection and in washing injection containers.

The process of the present invention is further available for removing pyrogens from an aqueous solution containing drug(s) for hematic administration. Examples of such an aqueous solution include those of various drugs which should be subjected to a pyrogen test according to The Pharmacopoeia of Japan, for example, fructose injection, physiological saline solution, dextran 40 injection, glucose injection, Ringer solution and sodium citrate injection for transfusion. The present invention may be applied to any drug for hematic administration, from which pyrogens should be removed during the process of the preparation thereof, without limitation.

PRIOR ART

A pyrogen, in particular an endotoxin which is a typical example thereof, originates from the cell wall of a gram-negative bacterium and comprises lipopolysaccharides. The molecular weight of lipopolysaccharides varies from thousands to tens of thousands depending on its bacterial origin. However, lipopolysaccharides are considered to be present as an associate which has relatively hundreds of thousands to millions of molecular weight in aqueous solution. When it enters into the body, even in an ultramicro amount, it can induce serious fever and sometimes cause death.

It has been recently disclosed that lipid A, which is a constituent of an endotoxin and has a molecular weight of approximately 2,000, is also pyrogenic.

The Pharmacopoeia of Japan obliges us to effect a pyrogen test on rabbits in order to detect endotoxins. Since every conventional pyrogen test involves a troublesome procedure and a prolonged period of time, there has been marketed a detection reagent by which endotoxins can be readily detected within a short period of time. This reagent takes advantage of a reaction between an endotoxin and limulus hemocytes whereby the hemocytes coagulate. Further there has been established a colorimetric method with the use of a synthetic substrate based on the reaction mechanism between an endotoxin and limulus hemocytes. Recently the detection limit of this colorimetric method has been further improved from the order of ng/ml to that of pg/ml. Thus it is now possible to detect an ultramicro amount of endotoxins.

Known processes for preparing a pyrogen-free solution from a pyrogen-containing stock solution include those in which a reverse osmotic membrane or an ultrafiltration membrane is employed. A reverse osmotic membrane, which is used in desalination, has a cut-off molecular weight of 500 or below. Thus, it enables the removal of lipopolysaccharides constituting endotoxins as well as lipid A, which is the terminal constituent thereof. However, the reverse osmotic membrane should be operated under elevated pressure, which causes a considerable leakage of the stock solution from a damaged part of the membrane and requires a large amount of energy.

On the other hand, an ultrafiltration membrane may be operated under lower pressure and thus requires less energy than the reverse osmotic membrane. However the former is inferior to the latter in the capability of removing endotoxins. Namely, the lipopolysaccharides of a high molecular weight can be removed by using an ultrafiltration membrane of a cut-off molecular weight of, for example, 30,000. However lipid A, which is the terminal constituent of the lipopolysaccharides and has a lower molecular weight, would permeate through. Therefore, it is necessary to employ an ultrafiltration membrane of a cut-off molecular weight of 5,000 or below, though the permeation rate thereof is lower than that of the ultrafiltration membrane having a fractionation or cut-off molecular weight of 30,000. In addition, an ultrafiltration membrane is damaged upon prolonged operation, which might cause the leakage of some portion of the endotoxins accumulated on the whole surface thereof from the damaged part. In order to overcome these disadvantages, two-step filtration is commonly employed. In this method, however, the removal efficiency in the first step is high but that in the second step is low.

BRIEF DESCRIPTION OF THE DRAWINGS

FIGS. 4 to 7 are each a schematic view of an example of the system of the present invention.

FIGS. 8 and 9 are each a schematic view of an example of the system of the present invention wherein two UF membranes are employed.

Figure 9:
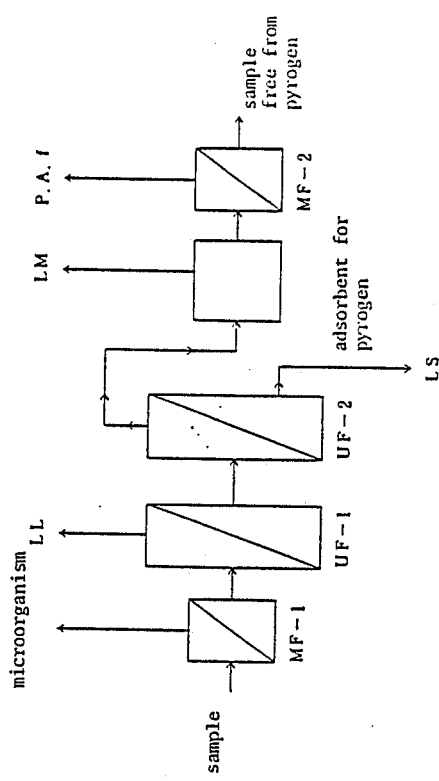

In the figures, a represents a stock solution, b and e represent each a pump, c represents an ultrafiltration membrane module, and d represents an adsorbent;

A represents a stock solution, B represents a regeneration solution, C represents a product solution, D is a regeneration waste, E is a waste and F is a receiver of the treated liquid.

1 represents a stock solution tank, 2 represents a regeneration solution tank, 3 represents a pyrogen adsorbent column, 4 represents a product solution tank, 5 represents an ultrafiltration membrane, 5' represents another ultrafiltration membrane, 6 represents a pump, 6' represents another pump, 7 represents a flow meter, and 11 to 20 represent each a valve.

SUMMARY OF THE INVENTION

Under these circumstances, the present inventors have conducted extensive studies in order to develop a process for removing pyrogens from a pyrogen-containing solution which is not accompanied by the problems as described above. As a result, they have found that a process for efficiently removing pyrogens can be established by using a membrane together with a pyrogen adsorbent, thus completing the present invention.

The process of the present invention comprises the removal of endotoxins of molecular weights of ten thousands to millions with the use of an ultrafiltration membrane having a fractionation molecular weight of 10,000 to 200,000, a large pore size and a high permeation rate and thus is highly effective; and then removing endotoxins of molecular weights of several tens of thousands or below, which cannot be removed by the above-mentioned ultrafiltration membrane, and/or lipid A, of a molecular weight of approximately 2,000, with the use of a pyrogen adsorbent. Accordingly, this process is advantageous in that endotoxins of high molecular weights can be removed by the pyrogen adsorbent when the ultrafiltration membrane might be damaged upon prolonged operation; and that the lipid A of a molecular weight of approximately 2,000 can be steadily removed throughout a prolonged operation. The process of the present invention is further available for the removal of pyrogens from an aqueous solution of a useful material of a low molecular weight of, e.g., thousands of daltons or below, which is capable of permeating through an ultrafiltration membrane.

In this case, the ultrafiltration membrane to be employed preferably has a cut-off molecular weight of 10,000 to 200,000 and an average pore size of 20 Å to 0.1 $\mu$m, still preferably 30 Å to 200 Å.

The process of the present invention is further available for the removal of pyrogens from an aqueous solution containing a drug for hematic administration. More precisely, endotoxins having higher molecular weights than that of the drug, such as associated lipopolysaccharides and bacteria, from which the endotoxins originate, are removed by using a membrane of a large pore size through which the drug can readily permeate. Then endotoxins of lower molecular weights and lipid A are selectively removed by the pyrogen adsorbent. Thus, all of the pyrogens contained in the drug solution can be efficiently removed. The membrane to be used in the above process should have such a pore size such that the drug can readily pass through while impurities, including endotoxins larger than the drug, and microorganisms can be removed thereby. For example, an appropriate UF membrane (ultrafiltration membrane) may be employed therefor.

Examples of the drug include blood preparations, enzyme preparations, recombined proteins, peptides, hormones and polysaccharides for drugs. Further various injections and infusions, such as dextran injection, fructose injection, glucose injection, Ringer solution and sodium citrate injection for transfusion, may be treated in the above mentioned manner.

When the drug is a compound having a molecular weight of 1,000,000 daltons or above, such as hyaluronic acid, a UF-membrane of a cut-off molecular weight (which means the lower limit of the molecular weight of a sample capable of passing through the membrane; the same will apply hereinafter) of 1,000,000 or above may be employed. When the drug is a compound having a molecular weight of 100,000 to 1,000,000 daltons, such as immunoglobulin, an UF membrane of a fractionation molecular weight of 1,000,000 or above may be employed.

When the drug is a compound having a molecular weight of 100,000 daltons or below, such as albumin, a membrane of a cut-off molecular weight of 100,000 or above may be employed. When the drug has a molecular weight of 10,000 daltons or below, a membrane of a cut-off molecular weight of 10,000 or above may be employed.

Further, a combination of two or more UF membranes may be employed. FIGS. 8 and 9 each show a system for removing pyrogens with the use of two UF membranes.

The two UF membranes in the system of FIG. 8 are located in the reverse order of those of FIG. 9. Either system may be selected depending on the drug and pyrogens contained therein.

The UF-1 used in these systems is a membrane having a fractionation molecular weight which enables a sample to permeate therethrough as described above. The optimum fractionation molecular weight should be determined depending on the molecular weight of the sample to be treated.

The UF-2 is a membrane having a fractionation molecular weight which prevents the sample from permeating therethrough. For example, when the sample is a compound of a molecular weight of 1,000,000 daltons or above, such as hyaluronic acid, it is possible to use a UF-2 having a cut-off molecular weight of 1,000,000 or below. When the sample is a compound of a molecular weight of 100,000 to 1,000,000 daltons, such as immunoglobulin, it is possible to use a UF-2 having a cut-off molecular weight of 100,000 or below. When the sample is a compound of a molecular weight of 10,000 to 100,000 daltons, such as albumin, it is possible to use a UF-2 having a cut-off molecular weight of 10,000 or below. When the sample is a compound of a molecular weight of 2,000 to 10,000 daltons it is possible to use an UF-2 having a cut-off molecular weight of 2,000 or below.

Thus the UF-2 having the optimum cut-off molecular weight should be selected depending on the sample, similar to the case of the UF-1.

As shown in FIGS. 8 and 9, two microfiltration membranes (MF membranes) may be located before and/or after the UF membranes depending on the sample, though these MF membranes are not always required in these systems. The MF-1 is employed in order to remove macromolecules, including cells of bacteria such as gram-negative ones, which might be obstacles for the treatment with the UF membranes, while the MF-2 is employed for removing minute pyrogen adsorbent fragments (P.A.f). It is preferable that each of these MF-1 and MF-2 membranes has a pore size of approximately 0.2 $\mu$m.

The symbols LS, LM and LL used in FIGS. 8 and 9 mean each the size of a pyrogen associate. A pyrogen generally forms associates having a certain molecular weight distribution in a solution. When treated with a membrane, therefore, it is divided into fractions of associates different in molecular weight from each other. Thus, these pyrogen associates are divided into types depending on size for convenience. Namely, a pyrogen associate of a molecular weight comparable to that of a sample is referred to as LM, while those larger and smaller than it are referred to as LL and LS, respectively.

The membranes to be used in the present invention may be made of a synthetic polymer such as polysulfone (PS), polyacrylonitrile (PAN) or polyamide or a semisynthetic polymer such as cellulose acetate. This modules thereof may be selected from among, for example, hollow fiber (HF) type, spiral type, pleated type, tubular type and plate and frame type.

Any pyrogen absorbent may be used in the present invention without limitation, so long as it can efficiently adsorb pyrogens. Preferably examples thereof include those obtained by immobilizing, for example, an amino acid, iminodiacetic acid or an antibiotic on a substrate comprising, for example, agarose or cellulose. Alternately, an adsorbent obtained by binding a nitrogenous heterocyclic compound such as L-histidine to a water-insoluble carrier (cf. Japanese Patent Laid-Open No. 183172/1982) or another one comprising hyaluronic acid and an anionic resin (cf. Japanese Patent Laid-Open No. 67024/1979).

Although the pyrogen-containing solution to be treated according to the present invention is not particularly restricted, those having an endotoxin concentration of $10^4$ ng/ml or below are particularly preferable.

Figure 1:
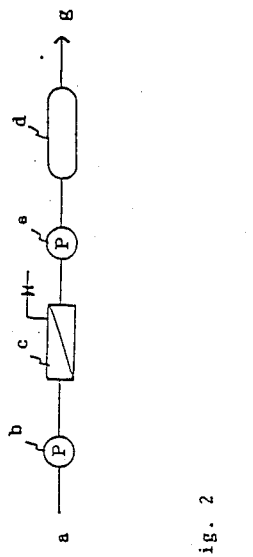
FIGS. 1 to 3 are each a schematic view of a preferable embodiment of the process of the present invention.
Figure 2:
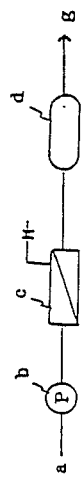
Figure 3:
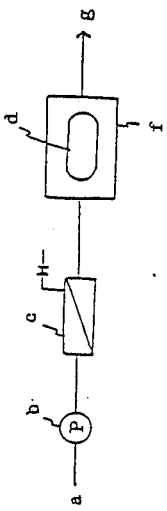

Referring now to the drawings, there are shown some preferable embodiments of the present invention. FIGS. 1 to 3 schematically each show a process for preparing a pyrogen-free solution from a pyrogen-containing stock solution.

The process of FIG. 1 may be employed when the packing ratio of the pyrogen adsorbent is high and the adsorbent column should be operated under elevated pressure. Namely, a stock solution a is pressurized with a pump b and passed through an ultrafiltration membrane module c to thereby give a permeating solution g. When the high packing ratio of the adsorbent d makes it impossible for the stock solution a to pass through the pyrogen adsorbent d under the membrane module pressure alone, a pump e is further provided before the adsorbent d to thereby repressurize the solution permeating through the ultrafiltration membrane module c. Then the solution is passed through the adsorbent d and the pyrogen-free solution g is obtained.

The process of FIG. 2 may be employed when the packing ratio of an adsorbent d is low and the permeation pressure is low. Namely, a stock solution is pressurized with a pump b and passed through the ultrafiltration membrane module c. The permeating solution thus obtained is then passed through an adsorbent d to thereby give the pyrogen-free solution g.

In the process of FIG. 3, an adsorbent is immersed in a reservoir for the solution permeating through an ultrafiltration membrane module. Namely, the solution passing through the ultrafiltration membrane module is temporarily stored in the reservoir f, similar to the process of FIG. 2, in which the adsorbent d is immersed. Thus the pyrogen-free solution can be prepared in the reservoir. Therefore the pyrogen-free solution g can be used continuously or at any time.

EXAMPLES

To further illustrate the present invention, the following Examples and Comparative Examples will be given.

COMPARATIVE EXAMPLE 1

A stock solution of an endotoxin concentration of 250 ng/ml was continuously treated with a polyacrylonitrile ultrafiltration membrane module having a cut-off molecular weight of 30,000 at a filtration efficiency of 90% for one week. Endotoxins were detected by subjecting the filtrate to two test methods, i.e., the limulus test with the use of Limulus HS Test Wako (mfd. by Wako Pure Chemicals Co., Ltd.) having a detection sensitivity of 0.01 ng/ml and the colorimetry with the use of Endospecy, trademark of Seikagaku Kogyo K.K., having a detection sensitivity of 1 pg/ml. As shown in the following Table, no endotoxin was detected by any of both methods until the second day. But endotoxins were detected by the colorimetry from the third day. On the fifth day, endotoxins were detected by both methods.

| | Day | | | | | |
|---|---|---|---|---|---|---|
| | 0 | 1 | 2 | 3 | 4 | 5 |
| Limulus HS Test Wako | — | — | — | — | — | + |
| Endospecie (pg/ml) | <1 | <1 | <1 | 1 | 3 | 11 |

<1: lower than the detection limit.

COMPARATIVE EXAMPLE 2

Polyacrylonitrile ultrafiltration membrane modules having a cut-off molecular weight of 80,000 were employed in two steps and the endotoxin removal efficiency of each module was evaluated. A stock solution of an endotoxin concentration of 250 ng/ml was treated with these modules. After the completion of each step, endotoxins contained in the treated solution were detected with the use of an Endospecy (mfd. by Seikagaku Kogyo K.K.). As shown in the following Table, the removal efficiency in the first step was 99.99% while that in the second step was 80%.

| | | Endotoxin conc. | Removal efficiency |
|---|---|---|---|
| First step: | inlet after permeation | $2.5 \times 10^5$ pg/ml<br>25 pg/ml | 99.99% |
| Second step: | inlet after permeation | 25 pg/ml<br>5 pg/ml | 80.0% |

EXAMPLE 1

The systems of FIGS. 1 to 3 were employed In each system, a stock solution of an endotoxin concentration of 250 ng/ml was continuously treated with a polyacrylonitrile ultrafiltration membrane module of a cut-off molecular weight of 30,000 at a filtration efficiency of 90%. Then the treated solution was passed through a pyrogen adsorbent comprising L-histidine immobilized on agarose. Subsequently endotoxins contained in the solution thus treated were detected colorimetrically. As shown in the following Table, no solution contained any detectable endotoxin.

| | Day | | | | | | | |
|---|---|---|---|---|---|---|---|---|
| System of | 0 | 2 | 4 | 6 | 8 | 10 | 12 | 14 |
| FIG. 1 | <1 | <1 | <1 | <1 | <1 | <1 | <1 | <1 |
| FIG. 2 | <1 | <1 | <1 | <1 | <1 | <1 | <1 | <1 |
| FIG. 3 | <1 | <1 | <1 | <1 | <1 | <1 | <1 | <1 |

<1: lower than the detection limit (1 pg/ml).

EXAMPLE 2

The procedure of Example 1 was repeated except that a physiological saline solution containing 50 ng/ml of endotoxins was used. The obtained results were the same as those of Example 1.

EXAMPLE 3

The procedure of Example 1 was repeated except that a fructose injection containing 50 ng/ml of endotoxins was used. The obtained results were the same as those of Example 1.

EXAMPLE 4

A test was conducted by using a human serum albumin (HSA) solution of an HSA concentration of 5% (determined from the UV absorbance at 280 nm), which had been adjusted to pH 6.5 and to an ion strength ($\mu$) of 0.01 with a phosphate buffer solution, as a sample. According to the limulus test, by using Limulus HS-Test Wako and a Toxinometer ET-201 (both mfd. by Wako Pure Chemicals Co., Ltd.) this solution contained approximately 1300 ng/ml of endotoxins.

100 ml of the sample solution was concentrated fivefold by treating the same with a pyrogen-free (1 pg/ml or less) polyether sulfone hollow fiber UF module (cutoff molecular weight: 100,000; FUS-1081, mfd. by Daicel Chemical Industries, Ltd.). The penetrating solution thus obtained contained 3.2% of HSA (HSA recovery: approximately 40%) and approximately 3 ng/ml of endotoxins.

The permeating HSA solution was then passed through a column packed with the same pyrogen adsorbent as used in Example 1 (i.e. 0.9 cm $\times$ 27.5 cm) at a flow rate, SV, of 2 (approximately 0.6 ml/min). The eluate thus obtained contained approximately 3% of HSA (HSA recovery after column treatment: approximately 94%) and approximately 0.016 ng/ml of endotoxins.

Therefore, the efficiency of removing pyrogens from the sample according to the process of the present invention was approximately 99.998%.

When the HSA in a sample is contaminated with bacteria, it is preferable to incorporate an MF-1 (microfiltration membrane) into the system for removing pyrogens (cf. FIG. 8). When there is a possibility that minute pyrogen adsorbent fragments (P.A.f.) might be eluted from the pyrogen adsorbent column, it is further preferable to incorporate an MF-2 (microfiltration membrane) into the system as the final filter.

System for removing pyrogens

As described above, the process for removing pyrogens of the present invention comprises combining filtration with an ultrafiltration membrane with adsorption with an pyrogen adsorbent. In the adsorption step, however, the capability of the pyrogen adsorbent will be lowered over time. When this capability falls below a threshold value, therefore, it is necessary to regenerate the adsorbent to thereby recover the capability thereof. However none of the known systems for effectively removing pyrogens involves such a means of regenerating a pyrogen adsorbent. Accordingly, it is another object of the present invention to provide a system for effectively removing pyrogens which involves a means of efficiently regenerating a pyrogen adsorbent.

This object can be achieved by using the system of the present invention.

Thus, the system of the present invention for removing pyrogens involves a means of removing pyrogens contained in a stock solution with the use of a pyrogen adsorbent, as well as another means of regenerating said adsorbent, with a regeneration solution.

It is preferable that this system involves a means for preliminarily removing pyrogens contained in the regeneration solution by using an ultrafiltration membrane. As the regeneration solution, an aqueous solution of a compound of a low molecular weight is generally employed. Examples thereof include aqueous solutions of sodium deoxycholate, sodium hydroxide and sodium chloride (cf. Japanese Patent Laid-Open No. 183712/1982). Thus pyrogens of higher molecular weights are exclusively removed from the regeneration solution by treating the same with an ultrafiltration membrane.

It is further preferable that this system involves a means for washing the pyrogen adsorbent with the regeneration solution flowing in the reverse direction. Namely, the regeneration solution is passed in the reverse direction of the flow of the stock solution in normal operation. Thus, the pyrogens adsorbed by the pyrogen adsorbent may be readily desorbed therefrom.

It is further preferable that the stock solution and the regeneration solution are fed into the system through a common pump. The normal operation for feeding the stock solution and the regenerating operation for feeding the regeneration solution are conducted one after another. Thus it is possible to feed these solutions through the same pump, which serves for the saving of one pump.

It is further preferable that the system involves a means of treating the regeneration waste with an ultrafiltration membrane and then recovering the same. Thus the loss of the expensive regeneration solution can be decreased.

Referring to the drawings, the system of the present invention will be described.

FIG. 4 is a schematic view of an example of the system of the present invention, wherein A is a stock solution; B is a regeneration solution; C is a product solution; and D is a regeneration waste. The stock solution in a stock solution tank 1 is fed into a pyrogen adsorbent column 3 via a pump 6 and a flow meter 7. After pyrogens contained in the stock solution are adsorbed by the pyrogen adsorbent, the resulting product solution is stored in a product solution tank 4. When the capability of the pyrogen adsorbent is lowered to a threshold value, the feed of the stock solution is ceased and the pyrogen adsorbent is regenerated. The regeneration solution, from which pyrogens have been preliminarily removed with an ultrafiltration membrane 5, is stored in a regeneration solution tank 2 and fed into the pyrogen adsorbent column 3 via the pump 6 and the flow meter 7. After regenerating the pyrogen adsorbent, the resulting regeneration waste is discharged out of the system.

FIG. 5 is a schematic view of another example of the system of the present invention. In this example, a pyrogen adsorbent is regenerated by a reverse washing method. A stock solution is fed into a pyrogen adsorbent column 3 via a pump 6. After removing pyrogens therefrom, the resulting product solution is stored in a product solution tank 4. When the pyrogen adsorbent is to be regenerated, the feed of the stock solution is ceased and a regeneration solution is fed into the pyrogen adsorbent column in the reverse direction ia a pump 6'.

FIG. 6 is a schematic view of still another example of the system of the present invention. In this example, the procedure of FIG. 5 is followed except that a stock solution and a regeneration solution are fed via a common pump. The stock solution flows through the sequence of stock solution tank 1→valve 11→pump 6→valve 13 pyrogen adsorbent column 3→valve 19→valve 14→product solution tank 4, while the regeneration solution flows through the sequence of regeneration solution tank 2→valve 12→pump 6→valve 18→pyrogen adsorbent column 3→valve 20→valve 17.

FIG. 7 is a schematic view of still another example of the system of the present invention. In this example, a regeneration waste is filtered through an ultrafiltration membrane and then recovered. A stock solution flows through the sequence of stock solution tank 1→valve 11→pump 6→valve 13→pyrogen adsorbent column 3→valve 14→product solution tank 4, while a regeneration solution flows through the sequence of regeneration tank 2→valve 12→pump 6→valve 13→pyrogen adsorbent column 3→valve 17→ultrafiltration membrane 5'. The filtrate is returned to the regeneration solution tank 2 while the residue is discharged out of the system as a waste E.

Thus the present invention provides systems for removing pyrogens from a solution whereby a pyrogen adsorbent can be efficiently regenerated.

We claim:

1. A process for the removal of pyrogens from a first solution containing said pyrogens and at least one other component comprising:
   (1) passing the solution through at least one membrane to obtain a second solution having a lowered pyrogen content, said at least one membrane having a different permeability for said pyrogens than for said at least one other embodiment; and
   (2) contacting said second solution with an adsorbent for said pyrogens to obtain a product solution which contains said at least one other component and is essentially pyrogen-free.

2. A process as claimed in claim 1, which comprises the steps of:
   (1) treating the first solution containing pyrogens with an ultrafiltration membrane having a cut-off molecular weight of 10,000 to 200,000 and having a large pore size and high permeation rate to water to remove pyrogens having molecular weights of ten thousands to millions; and
   (2) treating the second solution with a pyrogen adsorbent to remove endotoxins having molecular weights of up to several tens of thousands and lipid A having a molecular weight of about 2,000.

3. A process as claimed in claim 2, in which said ultrafiltration membrane has a pore size of 20 A to 0.1 micrometer on the average.

4. A process as claimed in claim 1, in which the first solution contains pyrogens and a pharmacologically effective ingredient and said at least one membrane has such a pore size that endotoxins having higher molecular weights than the ingredient may not pass through, but the ingredient may do so.

5. A process as claimed in claim 1, in which said at least one membrane has a pore size of 20 A to 0.1 micrometer on the average.

6. A process as claimed in claim 1 in which said first solution is passed through at least two membranes, one membrane being more permeable to said at least one other component than to said pyrogens and another membrane being more permeable to said pyrogens than to said at least one other component.

7. A process as claimed in claim 6, in which said first solution is passed through said one membrane before it is passed through said another membrane.

8. A process as claimed in claim 6, in which said first solution is passed through said another membrane before it is passed through said one membrane.

9. A process as claimed in claim 1, additionally comprising the step of passing said product solution through a membrane.

10. A process as claimed in claim 1, additionally comprising the step of regenerating said adsorbent for said pyrogens after the adsorption capability of said adsorbent has lowered to a threshold value.

11. A process as claimed in claim 10, in which said adsorbent is regenerated by a regeneration solution used in a reverse washing method.

12. A process as claimed in claim 11, in which said regeneration solution is passed through an ultrafiltration membrane before it is used in said reverse washing method.

13. A process as claimed in claim 1, in which said first solution contains endotoxins at a concentration of up to $10^4$ ng/ml.

14. A process as claimed in claim 1, in which said adsorbent for said pyrogens comprises L-histidine immobilized on agarose.

15. A process for the removal of endotoxins from a first solution containing said endotoxins at a concentration of up to $10^4$ ng/ml and at least one other component comprising:
   (1) passing the first solution through an ultrafiltration membrane having a cut-off molecular weight of 30,000 to obtain a second solution having a lowered endotoxin concentration; and
   (2) contacting said second solution with an adsorbent comprising L-histidine immobilized on agarose to obtain a product solution containing said at least one other component that is essentially endotoxin-free.

* * * * *